(12) United States Patent
Shawver et al.

(10) Patent No.: US 11,291,779 B2
(45) Date of Patent: Apr. 5, 2022

(54) AEROSOLIZATION DEVICE AND AN AEROSOL DRUG DELIVERY DEVICE

(71) Applicant: KONINKLIJKE PHILIPS N.V., Eindhoven (NL)

(72) Inventors: Michael Shawver, Brisbane (CA); Ryan Patton, Brisbane, CA (US); Lisa Molloy, Brisbane, CA (US); Matt Sander, Brisbane, CA (US); Ben Stedman, Brisbane, CA (US)

(73) Assignee: Koninklijke Philips N.V., Eindhoven (NL)

( * ) Notice: Subject to any disclaimer, the term of this patent is extended or adjusted under 35 U.S.C. 154(b) by 529 days.

(21) Appl. No.: 16/317,189

(22) PCT Filed: Jul. 13, 2017

(86) PCT No.: PCT/EP2017/067771
§ 371 (c)(1),
(2) Date: Jan. 11, 2019

(87) PCT Pub. No.: WO2018/011374
PCT Pub. Date: Jan. 18, 2018

(65) Prior Publication Data
US 2019/0298939 A1 Oct. 3, 2019

Related U.S. Application Data

(60) Provisional application No. 62/362,883, filed on Jul. 15, 2016.

(51) Int. Cl.
*A61M 11/00* (2006.01)
*A61M 15/00* (2006.01)

(52) U.S. Cl.
CPC .......... *A61M 11/003* (2014.02); *A61M 11/00* (2013.01); *A61M 15/0085* (2013.01);
(Continued)

(58) Field of Classification Search
CPC .. A61M 11/00; A61M 11/003; A61M 11/005; A61M 15/0085; A61M 2205/0294
See application file for complete search history.

(56) References Cited

U.S. PATENT DOCUMENTS 4,141,369 A * 2/1979 Burruss ................. A61M 15/00
131/330
4,303,083 A * 12/1981 Burruss, Jr. ........... A24F 40/485
131/271

(Continued)

FOREIGN PATENT DOCUMENTS

CN 102398398 A 4/2012
DE 102007012804 A1 * 9/2008 ........ A61M 15/0018
(Continued)

*Primary Examiner* — Kathryn E Ditmer
(74) *Attorney, Agent, or Firm* — Daniel H. Brean (57) ABSTRACT

An aerosolization device for providing aerosolized medicament to a user. The device has an aerosol generator at the base of a fluid receiving chamber. A top cover is provided over the top opening of the fluid receiving chamber, wherein the top cover defines a conduit opening which provides fluid access to the fluid receiving chamber. The top cover comprises a set of spokes which extend outwardly from the conduit opening and extend beyond the top opening thereby to seat the top cover over the outer housing. This top cover has a design which reduces the regions where liquid medication may become trapped.

13 Claims, 8 Drawing Sheets

(52) U.S. Cl.
CPC . *A61M 15/0021* (2014.02); *A61M 2205/0294* (2013.01); *A61M 2205/50* (2013.01); *A61M 2205/584* (2013.01); *A61M 2205/587* (2013.01); *A61M 2205/8206* (2013.01)

(56) References Cited

U.S. PATENT DOCUMENTS

| | | | |
|---|---|---|---|
| 4,755,413 A | 7/1988 | Morris | |
| 6,832,733 B2 | 12/2004 | Engel | |
| 7,344,783 B2 | 3/2008 | Shea | |
| 8,021,967 B2 | 9/2011 | Zhou | |
| 2002/0129812 A1* | 9/2002 | Litherland | A61M 11/005 128/200.14 |
| 2004/0089295 A1* | 5/2004 | Gallem | A61M 15/0015 128/203.12 |
| 2004/0227011 A1 | 11/2004 | Tseng | |
| 2005/0011514 A1 | 1/2005 | Power | |
| 2007/0089366 A1 | 4/2007 | Kasatshko | |
| 2009/0050138 A1* | 2/2009 | Hamaguchi | A61M 11/06 128/200.14 |
| 2009/0139888 A1* | 6/2009 | Berry | B65D 75/305 206/438 |
| 2010/0078013 A1* | 4/2010 | Power | B05B 17/0646 128/200.18 |
| 2012/0238702 A1 | 9/2012 | Beck | |
| 2013/0269684 A1* | 10/2013 | Patton | A61M 15/0065 128/200.16 |
| 2014/0020783 A1 | 1/2014 | Zazovsky | |
| 2014/0208978 A1 | 7/2014 | Sunder | |
| 2016/0001019 A1* | 1/2016 | Fink | A61M 15/002 128/200.14 |
| 2017/0043106 A1* | 2/2017 | Hyland | A61M 16/0833 |
| 2017/0232211 A1* | 8/2017 | Gallem | A61M 15/0065 128/203.12 |

FOREIGN PATENT DOCUMENTS

| | | |
|---|---|---|
| EP | 1439875 B1 | 11/2012 |
| WO | WO03020336 A2 | 3/2003 |
| WO | WO2012100100 A2 | 7/2012 |
| WO | WO2016003738 A1 | 1/2016 |

\* cited by examiner

AEROSOLIZATION DEVICE AND AN AEROSOL DRUG DELIVERY DEVICE

CROSS-REFERENCE TO RELATED APPLICATIONS

This patent application claims the priority benefit under 35 U.S.C. § 371 of international patent application no. PCT/EP2017/067771, filed Jul. 13, 2017, which claims the benefit under 35 U.S.C. § 119(e) of U.S. Provisional Application No. 62/362,883 filed on Jul. 15, 2016, the contents of which are herein incorporated by reference.

FIELD OF THE INVENTION

This invention relates to an aerosol delivery device.

BACKGROUND OF THE INVENTION

Aerosolization systems provide effective delivery for a variety of medicaments, such as insulin and asthma medications. Such systems deliver the medicaments directly to a user's respiratory system by aerosolizing a metered dose of the medicament in liquid form. The user then inhales the aerosolized medicament directly into the respiratory system, enabling faster treatment of various medical conditions.

Delivery of consistent and properly metered doses of aerosolized medicament to a user is very important. Current aerosolization systems often provide inconsistent doses by having some of the medicament remain in a reservoir in liquid form after the aerosolization process.

One particular issue is that liquid can remain trapped in edges defined between the reservoir main volume and a reservoir cap. For example as much as 50 microliters to 1 milliliter may remain, which may be as much as 30% of a dose.

Another issue is the formation of air bubbles above the mesh which interferes with medication reaching the aerosol generator, interrupting nebulization.

There is therefore a need for an aerosolization device which avoids liquid medicament being trapped in the fluid receiving chamber.

SUMMARY OF THE INVENTION

Examples in accordance with a first aspect of the invention provide an aerosolization device for providing aerosolized medicament to a user, the aerosolization device comprising:

a mouthpiece end by which a user may cause an inspiratory flow through a conduit;

an aerosol generator leading in to the conduit which includes a vibratable mesh;

a fluid receiving chamber leading into the aerosol generator for receiving a volume of a liquid medicament, wherein the fluid receiving chamber comprises a tapered chamber having a top opening and a smaller base opening for directing liquid medicament onto the vibratable mesh for aerosolization;

an outer housing; and a top cover over the top opening of the fluid receiving chamber, wherein the top cover defines an opening which provides fluid access to the fluid receiving chamber, wherein the top cover comprises a set of spokes which extend outwardly from the opening and extend beyond the top opening thereby to seat the top cover over the outer housing.

In this arrangement, the top cover of the fluid receiving chamber has a spoked design. This top cover defines an opening which is smaller than the top opening of the fluid receiving opening. However, instead of forming a continuous ring around the opening, the spokes reduce the regions where liquid medication may become trapped.

The top cover for example comprises an annular part which defines the opening, and the set of spokes extending outwardly from the annular part. The annular part forms a rigid opening through which medication can be provided. The spokes provide sufficient support for the annular part while also reducing the contact area with the top of the fluid receiving chamber.

The spokes may each extend radially outwardly. This provides a simple design. There may be between four and eight spokes, evenly angularly spaced around the conduit opening.

The fluid receiving chamber may comprise a set of ribs which extend from the top opening towards the base opening, with at least one rib at the angular location of each spoke.

These ribs further assist in reducing trapped liquid, by providing a flow path from the corner areas underneath the spokes.

Each rib may extend fully from the top opening to the base opening. There may be exactly one rib for each spoke.

These ribs further assist in reducing trapped air above the mesh, providing a flow path from the area above the mesh along the side of the base opening.

In an alternative design, the fluid receiving chamber comprises a set of channels which extend from the top opening towards the base opening, with at least one channel at the angular location of each spoke.

Again, each channel may extend fully from the top opening to the base opening. There may be exactly one channel for each spoke.

The device may comprise a cover over the fluid receiving chamber and vibratable mesh to keep out larger particles.

The top cover may further comprise a connecting band radially beyond the spokes and radially beyond the top opening. This provides a stronger structure without changing the functionality.

Another aspect of the invention provides an aerosol drug delivery device, comprising:

a main body having a first opening and a second opening;

an aerosolization device as defined above adapted to be removably received in the first opening, wherein the second opening aligns with the conduit opening when the aerosolization device is received in the first opening;

a battery or batteries in the main body; and a controller in the main body.

This defines the combination of the device defined above, which is a mouthpiece cartridge, and a receiving part which includes the controller and batteries. The main body may also include an external mouthpiece cover.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an aerosolization device for providing aerosolized medicament to a user. The device has an aerosol generator at the base of a fluid receiving chamber. A top cover is provided over the top opening of the fluid receiving chamber, wherein the top cover defines an opening which provides fluid access to the fluid receiving chamber through its center orifice. The top cover comprises a set of spokes which extend outwardly from the conduit opening and extend beyond the top opening thereby to seat the top cover over the outer housing. This top cover has a design which reduces the regions where liquid medication may become trapped.

The invention provides a modification which can be applied to known aerosolization devices. One example of known device will first be described, based on the disclosure of WO 2016/003738. FIGS. 1 to 6 are repeated from WO 2016/003738.

Figure 1:
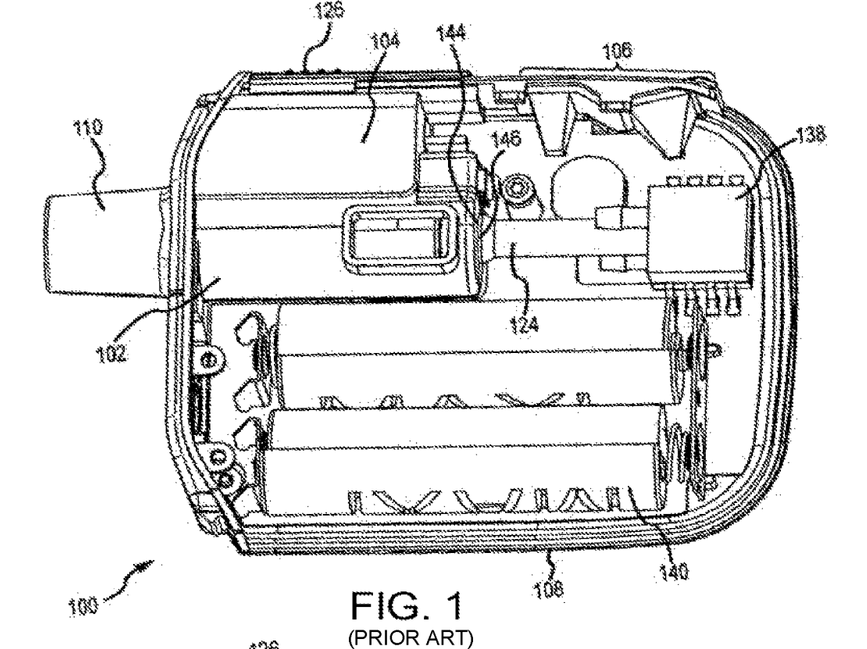
FIG. 1 shows an interior of an aerosolization device.
Figure 2:
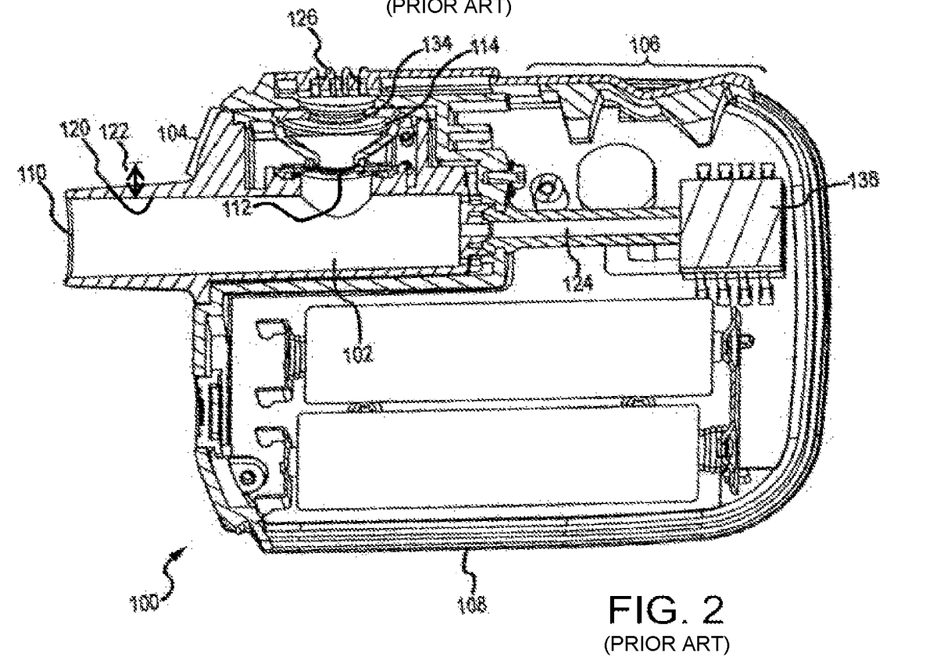
FIG. 2 shows a cross section of FIG. 1.

FIGS. 1 and 2 show an aerosolization device 100, which includes a conduit 102 and an aerosol generator 104 in communication with the conduit 102. The aerosolization device 100 also includes one or more indicator mechanisms 106, shown here as indicator lights. The one or more indicator mechanisms are coupled with a housing 108 or some other portion of device 100. Conduit 102 and aerosol generator 104 may also optionally be coupled with housing 108.

The conduit 102 includes a mouthpiece end 110 through which a user may inhale to produce an inspiratory flow to deliver aerosolized medicament to the user's respiratory system. As seen in FIG. 2, the conduit 102 defines an inner wall 120. The aerosol generator includes a vibratable mesh 112. Liquid medicament can be dispensed onto the vibratable mesh 112, either directly from a vial of liquid medicament or indirectly by being funneled onto the vibratable mesh 112 by tapered walls of a fluid receiving chamber 114.

The vibratable mesh 112 is vibrated via a mechanism controlled by a processor to aerosolize a volume of liquid medicament when a flow rate of the inspiratory flow is within an operating range of the aerosol generator 104.

When vibrated, the vibratable mesh 112 operates to produce a plume of aerosolized medicament within the conduit 102 such that the aerosolized conduit can be inhaled into the user's lungs.

The vibratable mesh is disposed at a distance 122 from the inner wall 120 of the conduit 102. For example, the vibratable mesh 112 may be disposed at a distance 122 between about 1 mm and 6 mm from the inner wall 120. The vibratable mesh 112 may define a plurality of apertures from which the aerosolized medicament is dispersed into the conduit 102. The plurality of apertures may include more than 500 apertures, each aperture having a diameter between about 1 and 8 μm. In other examples, the plurality of apertures may include more than 1000 apertures. The small size of the apertures in conjunction with the vibratable mesh 112 being offset from the conduit 102 helps ensure that the aerosolized medicament is uncontaminated.

The vibratable mesh 112 may be dome shaped and be vibrated by an annular piezoelectric element (not shown) that circumscribes the apertures. The diameter of the vibratable mesh 112 may be in the range from about 5 mm to about 8 mm. The vibratable mesh 112 may also have a thickness in the range from about 50 microns to about 70 microns. Typically, the vibratable mesh 112 will be vibrated at a frequency in the range from about 50 kHz to about 150 kHz to aerosolize the dose of liquid medicament.

The conduit 102 includes an opening 134 that provides access to the fluid receiving chamber 114. The opening 134 may have a diameter that is smaller than a diameter of a top of the fluid receiving chamber 114. Such geometry ensures that sides of a tip of a dispenser of liquid medicament cannot contact the walls of the fluid receiving chamber 114, and also provides a contact point for a shoulder of a dispensing mechanism to prevent the dispenser tip from contacting the vibratable mesh 112. By preventing such contact, the tip cannot contact a volume of liquid medicament within the fluid receiving chamber 114 and pull some of the volume out of the fluid receiving chamber 114 and/or contaminate the liquid medicament.

Figure 5:
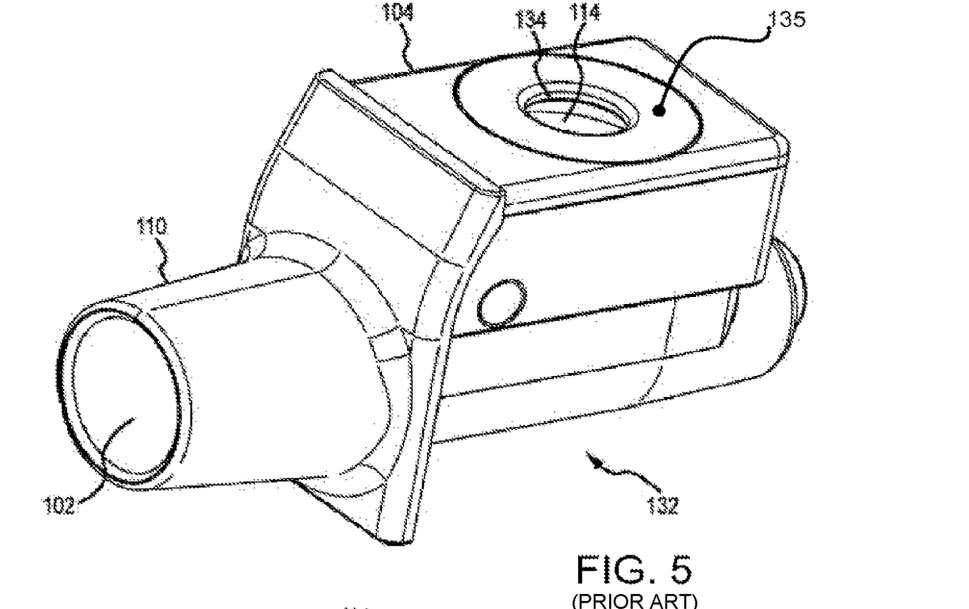
FIG. 5 shows the conduit and aerosol generator of the aerosolization device of FIG. 1 from the front.

The opening 134 is formed in a top cap 135 (shown in FIG. 5). The top cap provides a rim which defines the reduced diameter opening 134 compared to the top of the fluid receiving chamber 114.

The aerosolization device 100 includes a processing unit or integrated circuit (IC) 138 (shown in FIG. 2) that controls the function of or runs computer code to control other electronic components of the aerosolization device 100.

The aerosolization device 100, including IC 138, may be powered by batteries 140 that are coupled with IC 138. IC 138 may be electrically coupled with electronic components, such as any sensors, indicating mechanisms 106 and/or a piezoelectric element of aerosol generator 104. IC 138 controls the actuation of the indicator mechanisms and/or the aerosol generator 104 based on information received from any sensors, such as flow sensors or pressure transducers in fluid communication with the conduit 102.

The IC 138 may be electrically coupled with the conduit 102 and/or the aerosol generator 104 using a plug 124.

The conduit 102 and/or aerosol generator 104 are removable from housing 108. The conduit 102 and/or aerosol generator 104 may be inserted into housing 108 and interfaced with the tube 124 to provide access to inhalation flow rate sensing. Connections are also defined to electrical contacts to supply power to and control actuation of the aerosol generator 104 based on measurements from sensors in fluid communication with conduit 102.

Figure 3:
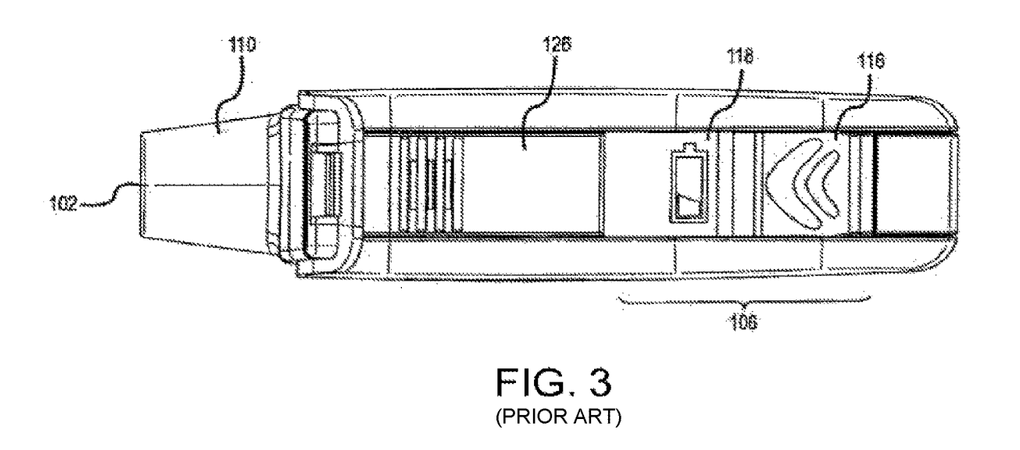
FIG. 3 shows a top of the aerosolization device of FIG. 1.

FIG. 3 shows a top view of the aerosolization device 100 and indicator mechanisms 106. The indicator mechanisms 106 for example include a breathing indicator 116 and a battery indicator 118. Breathing indicator 116 can direct a user when and how to breath to maximize delivery of the aerosolized medicament to the user's lungs. The breathing indicator 116 can include multiple indicators, such as various colored LEDs, to provide the user more detailed guidance. Breathing indicator 116 may be in the shape of a chevron that includes 3 colors of LEDs.

The optimal pulmonary delivery of medicaments such as liquid insulin occurs at specified flow rates and inspiratory times. For example, an optimal flow rate may be between about 5 and 14 L/min, or more often between about 7 and 14 L/min. Flow rates that are too high or too low can result in losses in the amount of aerosolized medicament delivered to the proper locations of a user's respiratory system. An optimal inspiratory time may be between 6 and 24 seconds. Breathing indicator 116 can be used to direct a user to maintain an inhalation within these parameters.

The breathing indicator 116 may produce a different colored light as an "end of dose" indictor to indicate that substantially all of the dose of medicament has been delivered. For example, a blue light may be emitted for a period of time, such as between about 1 and 10 seconds to alert the user that substantially all of the dose has been aerosolized and inhaled. Delivery of the entire dose may be predefined as when at least about 95% of the dose is delivered, more preferably 98% and most preferably when more than 99% of the dose is aerosolized. To receive the dose, the user may take several inhalations or a single inhalation depending on the volume of liquid drug to be delivered and the user's breathing capacity.

Each inhalation may be monitored by the device, with feedback provided to the user via indicator 116, to insure proper delivery to the lungs. The operation of the end of dose indicator may be delayed for a period, such as up to about 5 seconds after substantially all of the dose has been delivered, thus providing a "chaser" of air into the lungs. This chaser may serve to clear the upper airway and maximize the amount of the dose that is transported to the user's lungs.

A cover 126 is coupled with the fluid receiving chamber 114 and/or housing 108 to seal the fluid receiving chamber 114 and the vibratable mesh 112 when in a closed position. The cover 126 operates to prevent pathogens or other contaminants from entering the fluid receiving chamber 114. The cover 126 may operate to expose the fluid receiving chamber 114 and vibratable mesh 112 when in an open position. Cover 126 may include a sliding mechanism (not shown) such that the cover 126 may be moved from an open position to a closed position and back by sliding the cover 126 within or on a track.

Alternatively, the cover 126 is for example hinged such that the cover 126 may be flipped open and closed. A latching mechanism (not shown) may be included to maintain cover 126 in a closed position.

Figure 4:
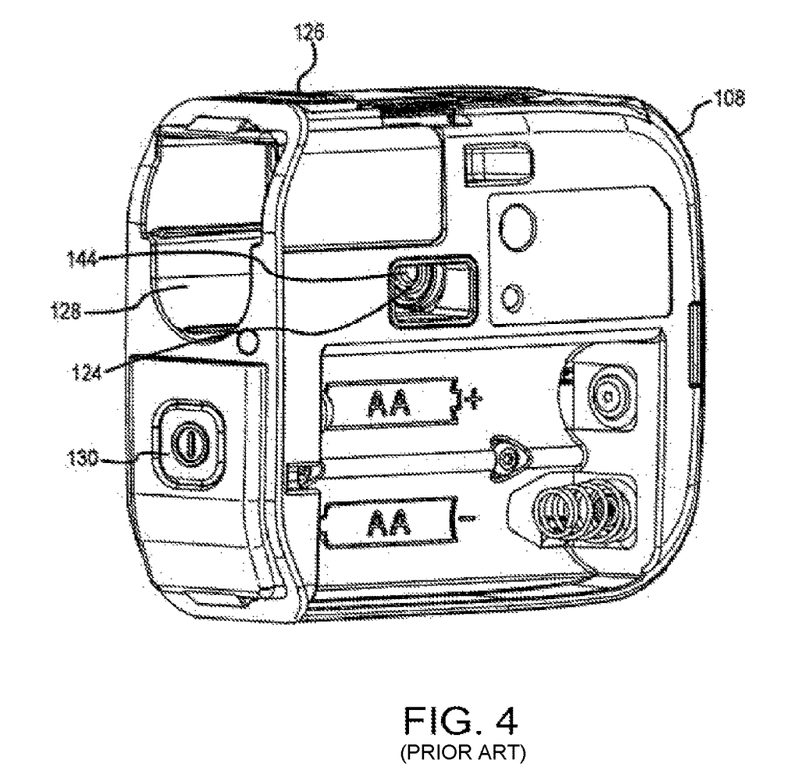
FIG. 4 shows the body of the aerosolization device of FIG. 1 with the conduit and aerosol generator removed.

One or both of conduit 102 and aerosol generator 104 are removably coupled with housing 108. FIG. 4 shows an isometric view of the aerosolization device 100 having the conduit 102 and aerosol generator 104 removed from an opening 128 within housing 108. The opening 128 may be configured to slidingly receive and secure one or both of conduit 102 and aerosol generator 104.

A power button 130 is shown for activating the aerosolization device 100.

The plug 124 is positioned within opening 128 to couple the conduit 102 and/or aerosol generator 104 with the IC 138. A male connector 144 (also shown in FIG. 1) of the plug 124 interfaces with the female connector 146 (shown in FIG. 1) of the conduit 102.

Figure 6:
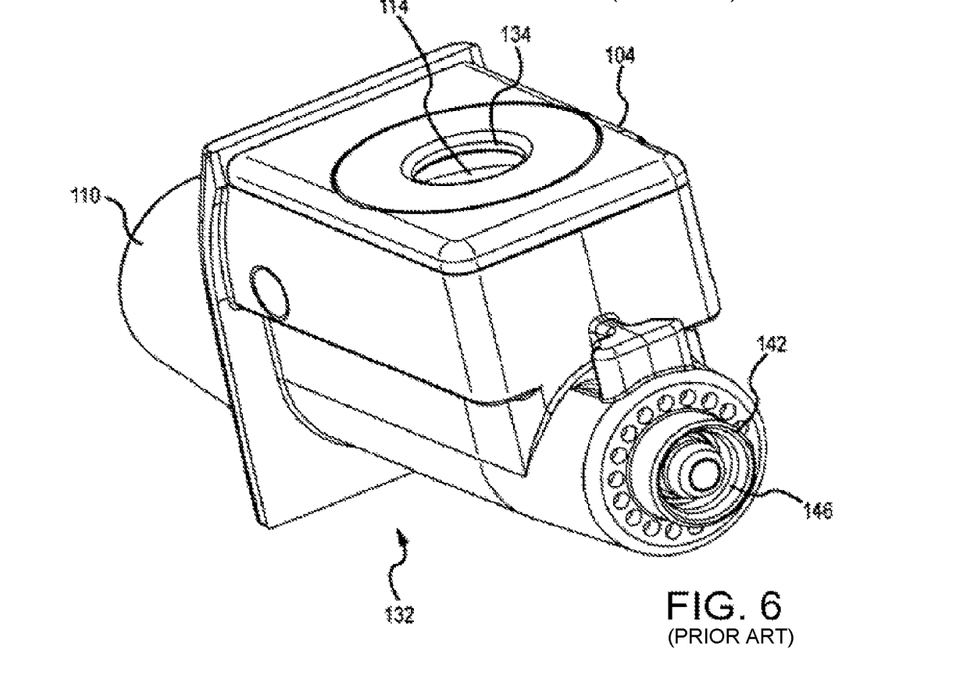
FIG. 6 shows the conduit and aerosol generator of the aerosolization device of FIG. 1 from the back.

FIGS. 5 and 6 show the conduit 102 and aerosol generator 104 removed from the housing 108. The conduit 102 and aerosol generator 104 may be separate components and/or share an exterior housing 132. The exterior housing 132 may be configured to slide into opening 128 of housing 108.

The exterior housing 132 may include an electrical connector 142, as shown in FIG. 6. The electrical connector 142 couples with the plug 124 as seen in FIGS. 1 and 2 to couple the conduit 102 and/or aerosol generator 104 to IC 138. The electrical connection 142 can include a female or male connection and couple with a corresponding connection on the plug 124. For example, the female connector 146 may interface with the male connector 144 of plug 124. In this manner, the exterior housing 132, aerosol generator 104, and/or conduit 102 may be removed for replacement while the housing 108, IC 138, and other components may be reused.

The electric and/or control components are often more expensive to replace than the exterior housing 132, aerosol generator 104, and/or conduit 102, so such reuse provides a cost effective solution when some components need to be replaced.

To the extent described above, the aerosolization device is known.

Figure 7:
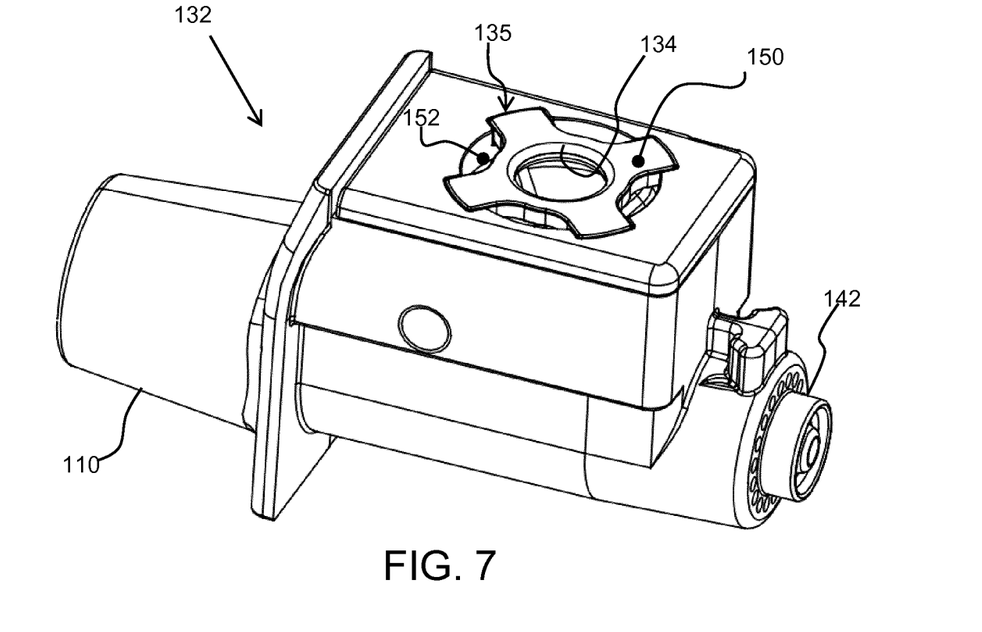
FIG. 7 shows a conduit and aerosol generator in accordance with an example of the invention.

FIG. 7 shows a modification to the conduit 102 and aerosol generator 104 assembly.

As explained above, the fluid receiving chamber 114 has a top cap 135, and this is then further closed by the cover 126 (as shown for example in FIG. 3). Insulin is hand pumped into the fluid receiving chamber 114 via a drop dispenser which registers and rests on the rim of the conduit opening 134 in the top cap 135 while being pumped.

The fluid receiving chamber 114 comprises a concave bowl and the top cap 135 of the known device is flat as is generally shown in FIG. 5. Insulin (or other medication) is drawn from the bottom of the fluid receiving chamber 114 via the action of the vibrating mesh aerosol generator.

After the fluid receiving chamber 114 is filled, a substantial amount of fluid can adhere in the corner region between the outer edges of the fluid receiving chamber and the top cap, where it remains throughout the treatment cycle. This renders the trapped volume of insulin (or other medication) unused, which is part of an intended dose, thereby reducing efficiency.

A first aspect relates to the design of the top cap 135.

FIG. 7 shows the top cap having a spoked design. Thus, instead of the top cap having an annulus form, there is a set of spokes 150 extending radially outwardly from the conduit opening 134. The spokes extend beyond the outer edge of the top opening of the fluid receiving chamber 114 so that they seat over the exterior housing 132. The spoked design effectively has notches 152 which extend radially inwardly from the outer edge of the top cap 135. This reduces surface area around the perimeter of the top cap, but leaves the spokes which are used to fasten and support the top cap 135.

The spokes break up the seam of contact between the top cap 135 and the walls of the fluid receiving chamber 114, reducing the available surface area for adhesion to occur.

Figure 8:
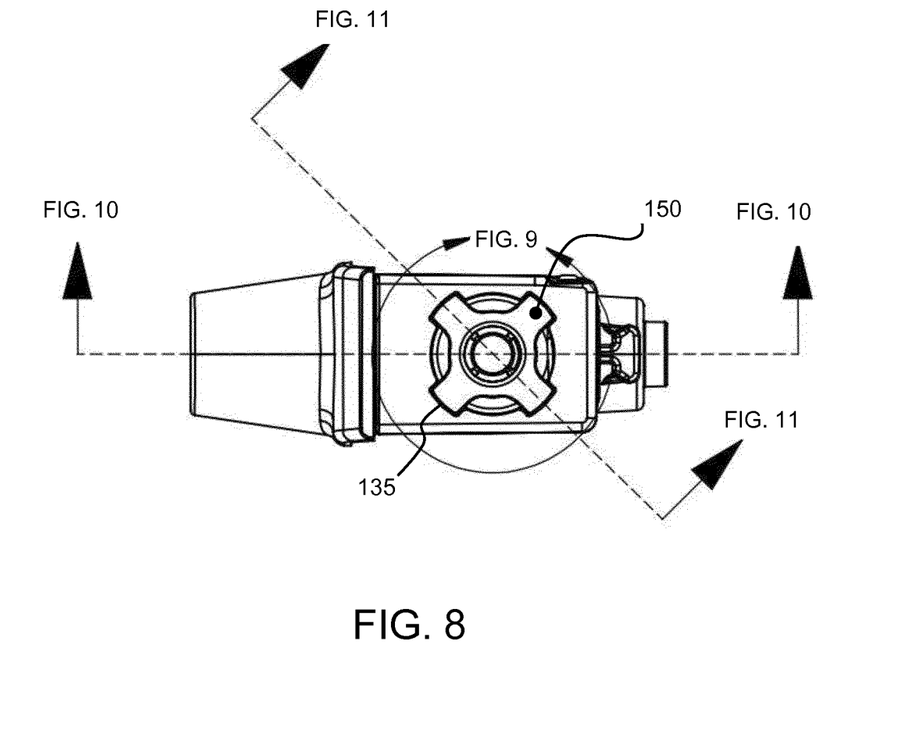
FIG. 8 shows the conduit and aerosol generator of FIG. 7 in plan view.
Figure 9:
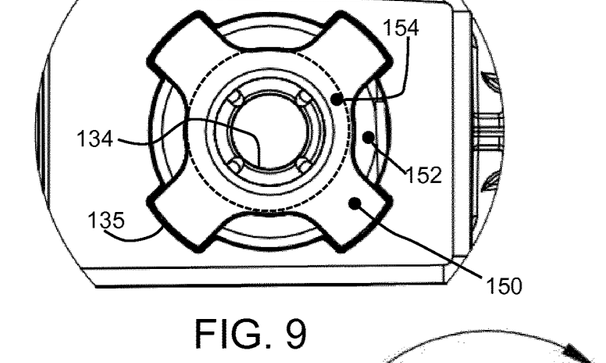
FIG. 9 shows the top view in more detail.
Figure 10:
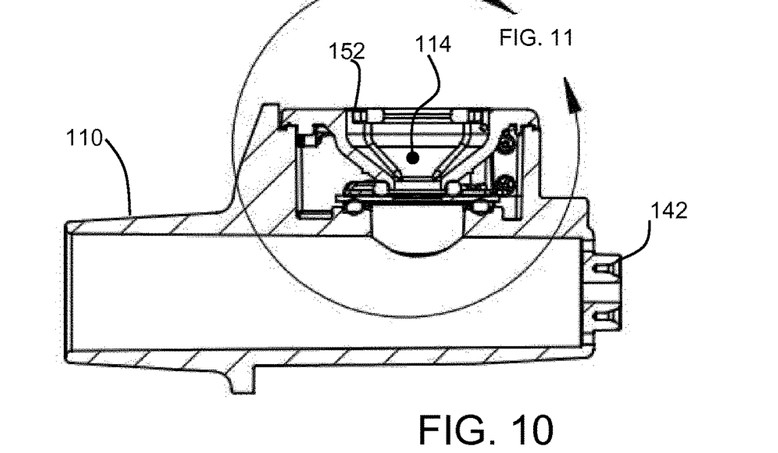
FIG. 10 shows a first cross section as identified on FIG. 8.
Figure 11:
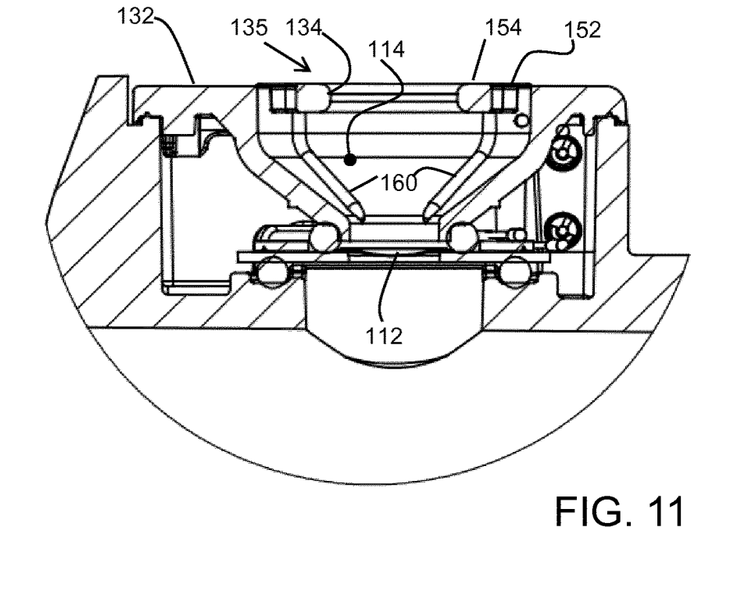
FIG. 11 shows an enlarged part of the cross section of FIG. 10.

FIG. 8 shows the design of FIG. 7 in plan view and is used to show how the images of FIGS. 9, 10 and 11 are formed.

FIG. 9 shows a close up view of the top cap 135, and shows the spokes 150 and notches 152. In the example shown, there are four spokes evenly spaced around the top cap, hence with 90 degrees between the spokes. There is an annular rim 154 around the conduit opening 134 before the spokes begin. Put another way, the notches extend radially inwardly, but not fully to the conduit opening 134 so that the conduit opening is fully formed with a surrounding rim 154.

There may be only three spokes, or indeed there may be more than four spokes. For example, there may be between 3 and 10 spokes. They are preferably evenly angularly spaced, but this is not essential.

FIG. 10 shows a cross section along the length of the conduit 102 and aerosol generator 104 assembly. This cross section passes along a pair of diametrically opposed notches. FIG. 11 is a close up view of FIG. 10.

The notches 152 are outside the annular rim 154, the inside of which defines the conduit opening 134. The top of the top cap 135 is flush with the top of the exterior housing 132.

The gaps left by the notches are closed by the cover 126 when the cover is closed.

Figure 12:
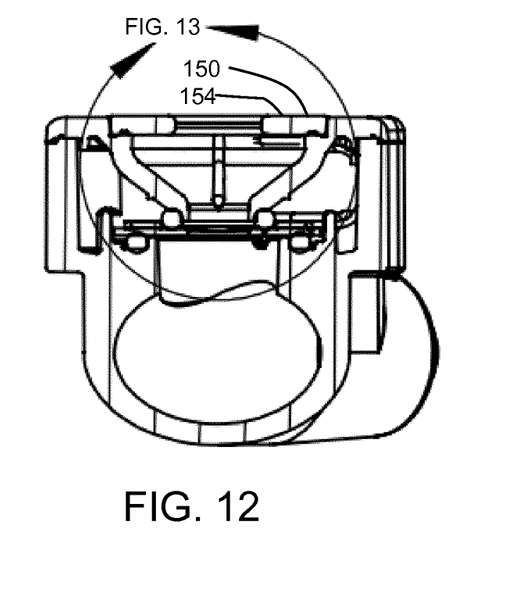
FIG. 12 shows a second cross section as identified on FIG. 8.
Figure 13:
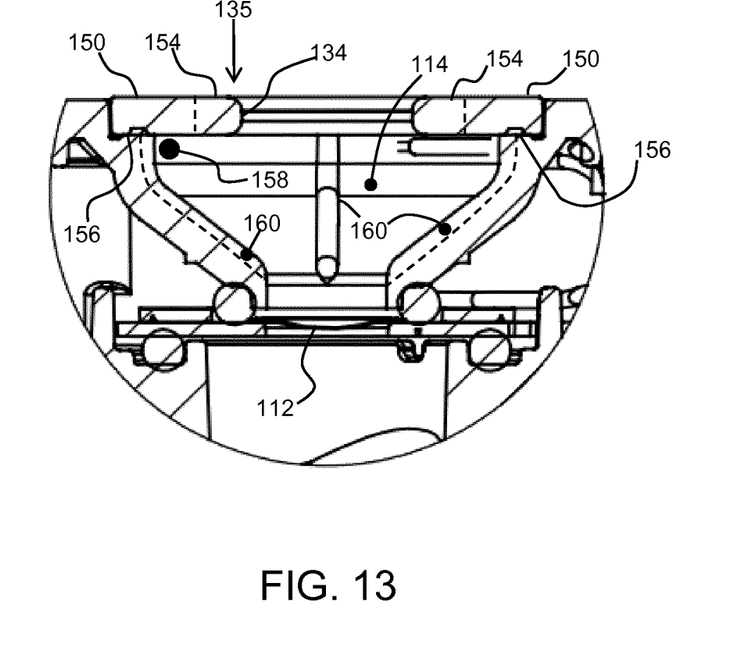
FIG. 13 shows an enlarged part of the cross section of FIG. 12.

FIG. 12 shows a cross section at an angle to the length of the conduit 102 and aerosol generator 104 assembly. This cross section passes along a pair of diametrically opposed spokes 150. FIG. 13 is a close up view of FIG. 12.

The spokes 150 sit on a recessed step 156 in the outer wall of the fluid receiving chamber 114 so that the top of the top cover 135 is flush with the exterior housing 132 as explained above.

A second aspect relates to the design of the fluid receiving chamber 114.

There remains an angled trap at the junction between each spoke 150 and the top of the fluid receiving chamber. This trap is shown for example as 158 in FIG. 13.

The second aspect provides the addition of thin ribs protruding from the inside face of the fluid receiving chamber 114, extending down from the top cap 135 to the vibratable mesh 112. The ribs act to wick down small amounts of fluid (insulin or other medicament) which adheres in the remaining sections of corner wedges where the multiple spoke arms sit over the top of the fluid receiving chamber.

These ribs 160 are shown in FIG. 13. Each spoke is associated with one rib which extends down the side of the fluid receiving chamber 114, and forms a projection which is proud of the surface of the fluid receiving chamber 114. Two ribs 160 can also be seen in FIG. 11.

The ribs may taper out before reaching the base of the fluid receiving chamber 114, or they may extend fully down to the bottom where the drain hole is formed. Furthermore, there may be more than one rib associated with each spoke 150. When a single rib is used for each spoke, it is for example angularly spaced at the center of each spoke.

Figure 14:
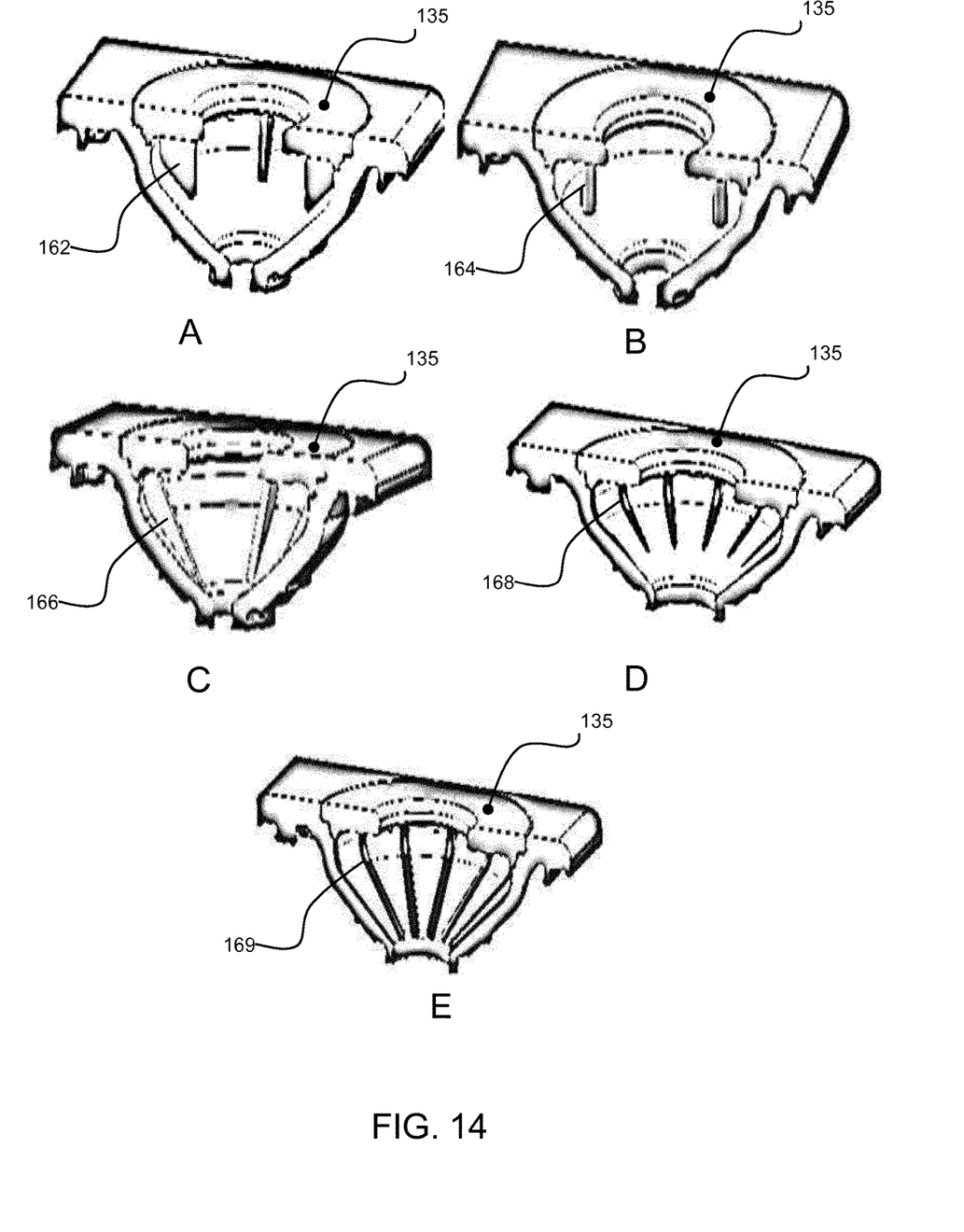
FIG. 14 shows some alternative rib designs.

The example above makes use of raised ribs running down the side of the fluid receiving chamber. There may be one rib per spoke or multiple ribs (e.g. 2) per spoke. Other designs are possible as shown in FIG. 14. Note that FIG. 14 does not show the spoked top cover and only shows alternative rib designs.

FIG. 14A shows that the ribs 162 may be part of the top cover, and hang down from the top cover.

FIG. 14B shows a variation with hanging pins 164 extending down from the top cover.

FIG. 14C shows more pronounced proud ribs 166 formed in the side wall of the fluid receiving chamber.

FIG. 14D shows a variation with recesses 168 instead of ribs, formed as channels in the side wall of the fluid receiving chamber. They extend only partially towards the base of the chamber in FIG. 14D. In FIG. 14E, these channels 169 extend fully to the base of the fluid receiving chamber.

Figure 15:
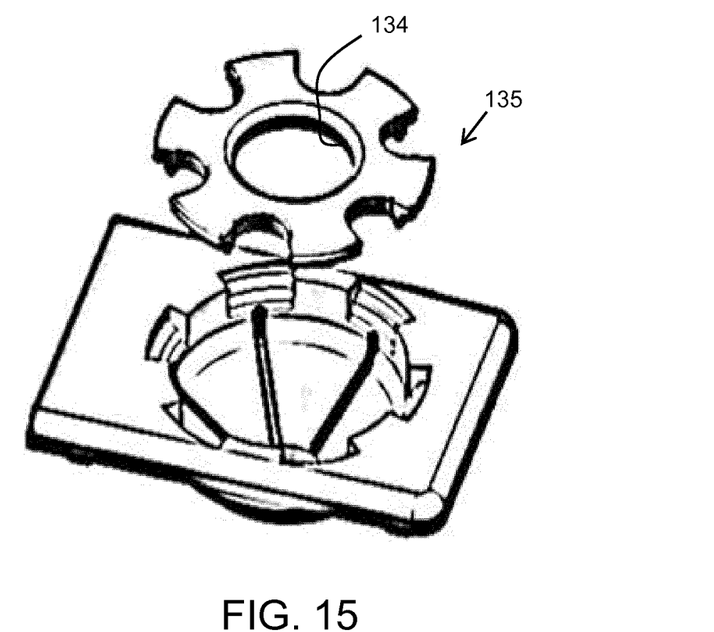
FIG. 15 shows a first alternative spoke design for the top cover.

There are also other spoke designs. FIG. 15 shows a variation with six spokes. They have a less uniform width than in the example above, being defined by U-shaped cut-outs into the outer circumference. At the outer periphery, the combined slot circumference is roughly equal to the combined spoke circumference, but more generally, the total spoke circumference may be between 20% and 60% of the total circular circumference. In the example of FIG. 15, the outer ends of the spokes are seated in notches, with one rib running down from each notch to the base of the fluid receiving chamber.

The spokes are separate where they sit over the radially outer edge of the top of the fluid receiving chamber. However, they may be connected again further out radially, as shown in FIG. 16.

Figure 16:
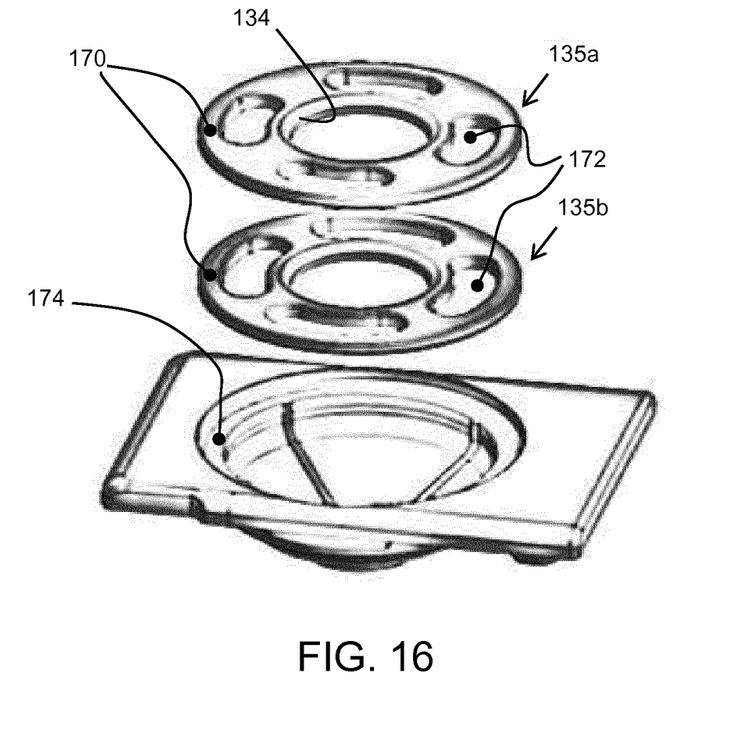
FIG. 16 shows a second alternative spoke design for the top cover.

FIG. 16 shows two possible designs 135a, 135b for the top cap. In each case, the spokes are joined together by an outer band 170 so that the spokes are formed by openings 172. The top cap sits over a rim 174 which is wider (radially) that the radial width of the outer band. Thus, a spoked design is present directly above the top opening of the fluid receiving chamber and the area for trapped liquid is accordingly reduced. The spokes thus still extend beyond the top opening, and they are rejoined further out. This gives a structurally stronger top cap design. The two designs 135a, 135b differ in the size of the openings, and correspondingly the sizes of the spokes.

Designs are shown with four and six spokes. There may be any number of spokes, although typically between four and eight (inclusive).

Various other specific designs of aerosol generator are known, as well ways to manufacture such aerosol generators and ways to supply liquid to the aerosol generators Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An aerosolization device for providing aerosolized medicament to a user, the aerosolization device comprising:
    a mouthpiece end by which a user may cause an inspiratory flow through a conduit;
    an aerosol generator leading into the conduit which includes a vibratable mesh;
    a fluid receiving chamber leading into the aerosol generator for receiving a volume of a liquid medicament, wherein the fluid receiving chamber comprises a tapered chamber having a top opening and a smaller base opening for directing liquid medicament onto the vibratable mesh for aerosolization;
    an outer housing; and
    a top cover over the top opening of the fluid receiving chamber, wherein an annular portion of the top cover defines a top cover opening which provides fluid access to the fluid receiving chamber, wherein the top cover comprises a set of spokes which extend outward from the annular portion of the top cover and extend beyond the top opening of the fluid receiving chamber thereby to seat the top cover over the outer housing.

2. An aerosolization device as claimed in claim 1, wherein the spokes each extend radially outwardly from the annular portion, each of the spokes being evenly angularly spaced around the annular portion.

3. An aerosolization device as claimed in claim 1, wherein there are between four and eight spokes, evenly angularly spaced around the annular portion.

4. An aerosolization device as claimed in claim 1, wherein the fluid receiving chamber comprises a set of ribs which extend from the top opening towards the base opening, with at least one rib at an angular location of each spoke.

5. An aerosolization device as claimed in claim 4, wherein each rib extends fully from the top opening to the base opening.

6. An aerosolization device as claimed in claim 4, wherein there is exactly one rib for each spoke.

7. An aerosolization device as claimed in claim 1, wherein the fluid receiving chamber comprises a set of channels which extend from the top opening towards the base opening, with at least one channel at an angular location of each spoke.

8. An aerosolization device as claimed in claim 7, wherein each channel extends fully from the top opening to the base opening.

9. An aerosolization device as claimed in claim 7, wherein there is exactly one channel for each spoke.

10. An aerosolization device as claimed in claim 1, further comprising a second cover over the fluid receiving chamber.

11. An aerosolization device as claimed in claim 1, wherein the top cover further comprises a connecting band radially beyond the spokes and radially beyond the top opening.

12. An aerosol drug delivery device, comprising:
a main body having a first opening and a second opening;
an aerosolization device as claimed in claim 1 adapted to be removably received in the first opening, wherein the second opening aligns with the top cover opening of the aerosolization device when the aerosolization device is received in the first opening;
a battery or batteries in the main body; and
a controller in the main body.

13. An aerosolization device for providing aerosolized medicament to a user, the aerosolization device comprising:
a mouthpiece end by which a user may cause an inspiratory flow through a conduit;
an aerosol generator leading into the conduit which includes a vibratable mesh;
a fluid receiving chamber leading into the aerosol generator for receiving a volume of a liquid medicament, wherein the fluid receiving chamber comprises a tapered chamber having a top opening and a smaller base opening for directing liquid medicament onto the vibratable mesh for aerosolization;
an outer housing; and
a top cover over the top opening of the fluid receiving chamber, wherein the top cover comprises a top cover opening which provides fluid access to the fluid receiving chamber and a set of spokes which extend outwardly from the top cover opening and extend beyond the top opening of the fluid receiving chamber thereby to seat the top cover over the outer housing, wherein the annular portion and the set of spokes define a substantially co-planar upper surface of the top cover;
wherein the fluid receiving chamber comprises a set of ribs which extend from the top opening of the fluid receiving chamber towards the base opening, with at least one rib at an angular location of each spoke.

* * * * *